United States Patent [19]

Ziemecki

[11] Patent Number: 5,151,543

[45] Date of Patent: Sep. 29, 1992

[54] SELECTIVE LOW PRESSURE HYDROGENATION OF A DINITRILE TO AN AMINONITRILE

[75] Inventor: Stanislaw B. Ziemecki, Wilmington, Del.

[73] Assignee: E. I. Du Pont de Nemours and Company, Wilmington, Del.

[21] Appl. No.: 708,945

[22] Filed: May 31, 1991

[51] Int. Cl.⁵ .................................. C07C 253/30
[52] U.S. Cl. .......................................... 558/459
[58] Field of Search .............................. 558/459

[56] References Cited

U.S. PATENT DOCUMENTS

| | | | |
|---|---|---|---|
| 2,208,598 | 7/1940 | Rigby | 260/464 |
| 2,257,814 | 10/1941 | Rigby | 260/464 |
| 2,762,835 | 9/1956 | Swerdloff | 260/465.5 |
| 3,322,815 | 5/1967 | Feldman et al. | 260/465.5 |
| 3,953,511 | 4/1976 | Frech et al. | 558/459 X |
| 4,389,348 | 6/1983 | Diamond et al. | 260/465.5 |
| 4,601,859 | 7/1986 | Galle et al. | 558/459 |

FOREIGN PATENT DOCUMENTS

| | | |
|---|---|---|
| 681932 | 4/1966 | Belgium . |
| 836938 | 7/1949 | Fed. Rep. of Germany . |
| 848654 | 7/1949 | Fed. Rep. of Germany . |
| 954416 | 12/1956 | Fed. Rep. of Germany . |

OTHER PUBLICATIONS

F. Mares et al, J. Catl., 112: 145-156 (1988).

*Primary Examiner*—Joseph Paul Brust
*Attorney, Agent, or Firm*—Linda A. Floyd

[57] ABSTRACT

Selective hydrogenation of aliphatic dinitriles to aminonitriles is achieved under low pressure with high yield preferably using a Raney nickel or Raney colbalt-containing catalyst.

14 Claims, 4 Drawing Sheets

SELECTIVE LOW PRESSURE HYDROGENATION OF A DINITRILE TO AN AMINONITRILE

FIELD OF THE INVENTION

This invention relates to a low-pressure process for the manufacture of aminonitriles. More particularly, the invention relates to a convenient low-pressure process for the selective partial hydrogenation of dinitriles. The process gives a high yield with high selectivity and high conversion of the starting material through use of a Raney catalyst at moderate temperatures and with either an excess of liquid ammonia or an alcohol solvent containing an inorganic base.

BACKGROUND OF THE INVENTION

With few exceptions, the hydrogenation of aliphatic dinitriles, NCRCN (I), is usually carried out to completion, i.e., with addition of 4 mol of hydrogen per mol of dinitrile, in order to prepare the corresponding diamines, $H_2NCH_2RCH_2NH_2$ (II). These are used, among other applications, in production of various polyamides. Thus, for example, adiponitrile is hydrogenated to hexamethylenediamine, one of the two monomers required in the production of Nylon 6,6; methylglutaronitrile is hydrogenated to methylpentamethylenediamine and/or 3-methylpiperidine; and dodecanedinitrile is hydrogenated to dodecamethylenediamine.

The preparation of linear aminonitriles by hydrogenation of the corresponding dinitriles is known. U.S. Pat. Nos. 2,208,598 (1940) and 2,257,814 (1941) to Rigby of E.I. du Pont de Nemours and Co. disclose nickel-on alumina and cobalt-containing catalysts in liquid ammonia and teach away from the use of nickel as a catalyst.

A development by Swerdloff (U.S. Pat. No. 2,762,835 (1956)) carries out the essential reaction in a mixed organic solvent, such as methyal (i.e., dimethoxymethane), dioxane, tetrahydrofuran, or methyl cyclohexane, which is inert to hydrogen; the reaction is terminated after at least 40% and before more than 65% of the dinitrile originally present is reacted. A specified method of practicing the invention involves using a hydrogenation catalyst of the ferrous metal group. An organic solvent is used and the reaction is conducted in the presence of anhydrous ammonia. Unreacted dinitrile must be distilled or extracted from the aminonitrile.

The use of Raney nickel and Group VIII metal catalysts in solvents such as benzene and toluene are disclosed in German Pats. 836,938 (1952) and 848,654 (1952), both issued to BASF.

Selectivity to aminonitriles can be achieved using Rh/MgO catalyst, as disclosed in U.S. Pat. Nos. 4,389,348 (1983) and 4,601,859 (1986), both to Allied Corporation, and in a paper "Preparation and Characterization of a Novel Catalyst for the Hydrogenation of Dinitriles to Aminonitriles", F. Mares, J. E. Galle, S. E. Diamond, and F. J. Regina, J. Catl. 112:145–156 (1988). However, the high price of rhodium makes this approach expensive.

The preparation of branched aminonitriles by hydrogenation of the corresponding dinitriles is described in U.S. Pat. No. 3,322,815(1967) and Belg. Pat. No. 681.932 (1966) both issued to National Distillers. These disclose the preparation of 5-amino-2-methylvaleronitrile using a nickel, cobalt, or ruthenium metal catalyst, liquid ammonia or a tertiary alkyl amine and an alkanol solvent. The latter patent describes a two-step process from compounds such as 2-methyleneglutaronitrile.

SUMMARY OF THE INVENTION

It is an object of this invention to provide a process of selective partial hydrogenation of aliphatic dinitriles. In one aspect of the invention the process includes (i) hydrogenating a dinitrile over a Raney-type catalyst selected from the group consisting of Raney nickel, nickel promoted with metals or metal oxides selected from Group VIB and ferrous metals of Group VIII of the Periodic Table, and Raney cobalt; (ii) monitoring the reaction of step (i); and isolating the product aminonitrile from the reaction mass before complete conversion of the dinitrile to the diamine. In another aspect of the invention, the dinitrile is hydrogenated in a stirred reactor at temperatures of between about 25 and 150° C., and at hydrogen pressures between about 50 and 2000 psi (0.345 and 13.79 MPa) in the presence of at least a 2:1 excess (ratio of solvent to dinitrile) of a solvent, which can be either liquid ammonia or an alcohol of from one to four carbon atoms and containing an inorganic base. A Raney-type catalyst is used and is selected from the group consisting of Raney nickel, Raney nickel promoted with metals or metal oxides selected from Group VIB and ferrous metals of Group VIII of the Periodic Table, and Raney cobalt. The resulting aminonitrile is recovered as the major product. A further object of this invention is the efficient and useful process for the partial conversion of the dinitrile, adiponitrile, with high selectivity and high yield to 6-aminocapronitrile in an aliphatic alcohol containing an inorganic base or in liquid ammonia and using a promoted Raney nickel catalyst. A still further object is a continuous format for the process.

BRIEF DESCRIPTION OF THE DRAWINGS

Various other objects, features, and attendant advantages of the present invention will be more fully appreciated when the present invention is considered in conjunction with the accompanying drawings.

DETAILED DESCRIPTION OF THE INVENTION

Figure 1:
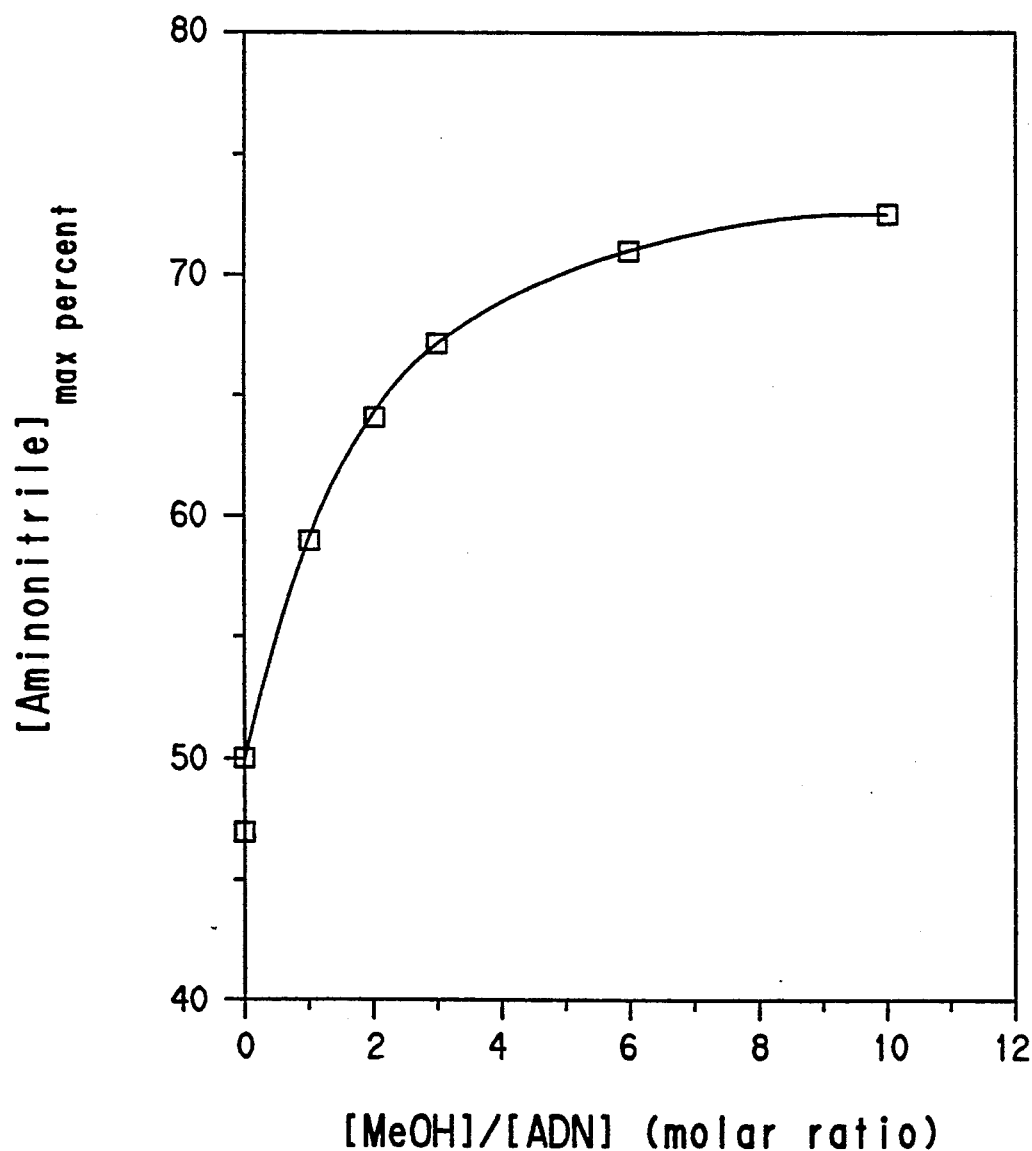
FIG. 1 shows the effect of dilution of adiponitrile (AND) with methyl alcohol (MeOH) on the maximum yield of 6-aminocapronitrile. Experimental conditions used the maximum amount of aminonitrile as a function of the MeOH to ADN molar ratio.

A convenient, low-pressure process resulting in high yield of aminocapronitrile or other aminonitriles at low levels of fully hydrogenated products and byproducts would be of great usefulness for commercial scale production of such compounds.

The present invention relates to a convenient, low pressure method of selective partial hydrogenation of a dinitrile (e.g., adiponitrile) to an aminonitrile (e.g., 6-aminocapronitrile). Half-hydrogenated products $NCRCH_2NH_2$ (III) obtained by Applicant by addition of 2 mol of hydrogen to the starting dinitrile (I), as for example 6-amino-capronitrile derived from adiponitrile, among other applications can be directly polymerized to yield corresponding polyamides, vis. Nylon 6.

The present invention enables the selective practical hydrogenation of aliphatic dinitriles containing from 3 to about 12 carbon atoms to corresponding aminonitriles. Preferably the carbon atoms are arranged in a branched or linear chain. Thus, for example, hydrogenation of adiponitrile to 6-aminocapronitrile, methylglutaronitrile to two isomeric aminonitriles (5-amino-2-methyl-valeronitrile and 5-amino-4-methyl-valeronitrile), and dodecanedinitrile to the corresponding aminonitrile.

An object of the invention is to maximize the formation of 6-aminocapronitrile to simplify the production of Nylon 6. In Applicant's instant process the yield of aminonitrile is much higher than that of the diamine for conversions of the starting dinitrile at least up to 90%. The desired intermediate can be extracted at the point in the reaction when it reaches its highest concentration and further converted to such compounds as Nylon 6 or hexamethylenediamine (HMD). This selectivity is a clear advantage over previous methods. In addition, the present invention demonstrates that selectivities to omega-aminonitriles approaching those claimed for the rhodium catalyst can be achieved by using relatively inexpensive Raney metal catalysts.

This result can be accomplished by carrying out the hydrogenation in an excess of liquid ammonia or in alcohols containing inorganic base in order to control the formation of byproducts, at temperatures from about 25 to 150° C., and at a total pressure from 50 to 2000 psi (0.345 to 13.79 MPa).

The aminonitrile produced in such a way can be directly polymerized to polyamides, or can be added to mixtures and polymerized to other nylon polymers and co-polymers. More particularly, the process enables direct polymerization of 6-aminocapronitrile to Nylon 6.

Starting Materials

The starting material may be any aliphatic dinitrile containing from 3 to about 12 carbons, but preferably containing from 6 to 12 carbon atoms such as adiponitrile (ADN), methylglutaronitrile (MGN), or dodecamethylenedinitrile (DDN). Adiponitrile, methylglutaronitrile, and dodecamethylenedinitrile are especially preferred. The process can be run using neat starting materials, but the preferred mode of operation is to carry out the hydrogenation in an appropriate solvent in excess greater than 2:1 (solvent-to-dinitrile).

Catalyst

Convenient and inexpensive hydrogenation catalysts are Raney nickel and Raney cobalt, active, porous materials produced by selectively dissolving a soluble component, such as aluminum or zinc, from an alloy of nickel or cobalt and the soluble component.

The instant reaction can be carried out over commercially available Raney nickel catalysts, including Raney Ni modified by the presence of other metals or metal oxides selected from Group VIB and from ferrous metals of Group VIII of the Periodic Table, and over Raney cobalt. (Group VIB includes Cr, Mo and W. Group VIII includes Fe, Ru, Os, Rh, Ir, Ni, Pd, and Pt.) Especially advantageous for the purpose of obtaining high selectivity to aminonitrile at a reasonable rate are: Raney nickel modified by chromium or by a combination of chromium and iron (e.g., W. R. Grace RNi 2400, or Activated Metals Co. Catalyst 4000), and cobalt-modified Raney nickel (e g , Degussa Co. BN 113 W).

The amount of catalyst added to the reaction medium is experimentally determined by consideration of the type of dinitrile being hydrogenated and the desired rate of the process under the temperature and pressure conditions applied. In general the amount of the Raney-type catalyst is from 0.5 to 50% by weight of the dinitrile to be hydrogenated and preferably from 5 to 20%.

Solvents

The selectivity to aminonitriles in the title reaction is enhanced by use of a solvent. Liquid ammonia, in amounts greater than 1 mol per mole of the dinitrile (and preferably greater than 2 mol per mole of the dinitrile), can be used as such a solvent (See Example 1). Aliphatic alcohols containing from one to four carbon atoms, used in amounts greater than 1 mol per mole of the dinitrile (and preferably greater than 3 mol per mole of the dinitrile) and in conjunction with either ammonia or an inorganic base, form another group of acceptable solvents. Other solvents were tested (See Example 6 for tetraglyme (2,5,8,11,14-pentaoxapentadecane) and Example 7 for tetrahydrofuran as solvents), but were found less advantageous than the preferred ones. The effect of dilution of a dinitrile with one of the preferred solvents on the maximum observed yield of the aminonitrile is illustrated in FIG. 1 for the case of adiponitrile being hydrogenated in methyl alcohol (with sodium hydroxide as a source of base). As seen in FIG. 1, the maximum yield of 6-aminocapronitrile initially increases with dilution, but seems to reach saturation above 10:1, [MeOH]:[ADN]molar ratio.

Bases

Presence of an inorganic base, such as alkali metal hydroxides, methoxides, or carbonates, or alkaline earth metal hydroxides, methoxides, or carbonates, is required when aliphatic alcohols are used as solvents, but not when liquid ammonia is the solvent. Preferred bases are ammonia, lithium hydroxide, sodium hydroxide, and potassium hydroxide. The most preferred base is liquid ammonia. The chosen base should have the pKb value of at most 5 and should be soluble in medium for the hydrogenation reaction. It was found to be beneficial to have between 1 and 10 wt% (relative to the amount of hydrogenated dinitrile) of such base present in the reaction mixture. As seen from Examples 2 and 3, increased concentration of the base accelerates the rate of dinitrile conversion and improves selectivity to the aminonitrile by limiting the amount of undesirable byproducts. In the absence of an inorganic base in the reaction mixture (see Example 8), the hydrogenation process is slow, and increased amounts of undesired products of condensation are found.

Temperature

Figure 2:
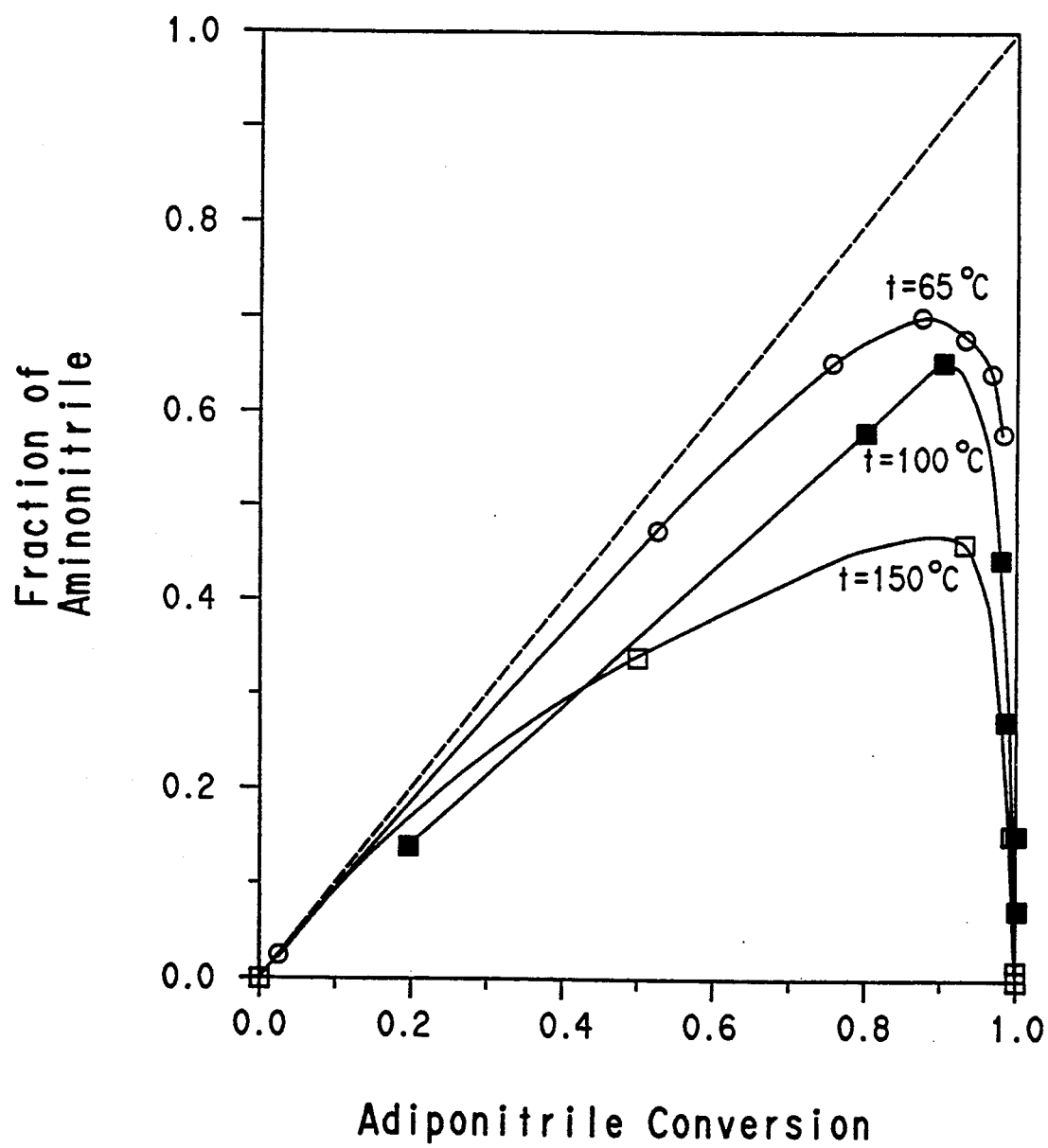
FIG. 2 shows the effect of temperature (t in ° C.)on the yield of 6-aminocapronitrile from the adiponitrile. The data show the fraction of aminonitrile as a function of adiponitrile conversion at three different temperatures.

The instant reaction can be operated from 25 to 150° C.; the preferred range of temperatures is from 50° to 80° C. At lower temperatures, the rate of hydrogenation reaction is too slow, and temperature control of the exothermic process becomes too involved to be practical. At higher temperatures, rates of hydrogenation of both the dinitrile and the aminonitrile are greatly accelerated. This makes it difficult to determine precisely the holdup time required for maximum aminonitrile concentration to be reached. The higher temperature also lowers selectivity to aminonitrile. In addition, increased formation of condensation products is observed at higher temperatures, resulting in lower selectivity to aminonitriles. The dependence of the yield of aminonitrile on conversion of the starting dinitrile at various temperatures is shown in FIG. 2.

Pressure

The low pressure aspect of this invention offers advantages in lower engineering costs compared to the high pressure industrial operation required by currently practiced methods. Additionally, the low pressure does not accelarate the reaction rate, which is useful in determining the optimum point of selectivity of the desired products.

The instant hydrogenation method can operate under pressures of hydrogen ranging from that pressure sufficent to maintain an acceptable forward movement in the production line to pressures of less than about 2000 psi (13.79 MPa). However, the preferable range of operational pressure is from about 250 to 1000 psi (1.72 to 6.89 MPa).

Contact Time of Reaction

The desired product of the title reaction, aminonitrile, is an intermediate in the process of hydrogenation of dinitriles to diamines. Its concentration in the reacting mixture passes through a maximum as the reaction progresses. The main objective of this invention is to maximize the concentration of the aminonitrile in the reacting mixture, at the highest possible conversion of the starting dinitrile. The yield of the aminonitrile, and the position of the maximum with respect to dinitrile conversion, depend on operating conditions such as temperature, hydrogen pressure, amount and kind of catalyst, dilution of starting dinitrile, amount of inorganic base added, as well as on the kind of solvent. These variables influence the optimum contact time for the reaction in ways that are understood by those skilled in the art. Additionally, FIGS. 1–4 provide useful guidance in choosing the parameters of several of these variables.

Commerical Considerations

The process of the invention can be operated batchwise or continuously in an appropriate reactor. Stirring or agitation of the reaction mixture can be accomplished in a variety of ways known to those skilled in the art. It is essentially the partial hydrogenation of the starting dinitrile to the corresponding aminonitrile over a promoted Raney catalyst, and with high selectivity achieved at high conversion of the dinitrile in a solvent selected, that makes this process efficient and useful.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characterisitcs of this invention, and without departing from the spirit and scope thereof, can make various changes and modifications of the invention to adapt it to various usages and conditions. All such modifcations are intended to fall within the scope of the appended claims.

Example 1

A 300 cc autoclave, equipped with a stirrer and a dip tube to allow sampling of its content, was charged with 60 g (0.55 mol) of adiponitrile, 0.4 g cyclododecane (internal standard for GC analysis), and 7 g Raney Ni 2400 (W. R. Grace Co) catalyst. The autoclave was flushed with nitrogen, and 100 cc (3.6 mol) of liquid ammonia was introduced; the autoclave was then heated to 80° C. The autoclave was connected to a source of hydrogen kept at 1000 psi (6.89 MPa); the rate of agitation was increased to 2000 rpm, and the first sample was taken. Subsequent samples were withdrawn every 30 min and analyzed by GC in order to construct concentration profiles of the main reaction components. Complete conversion of the starting dinitrile was obtained within 2 h on stream. At 70% adiponitrile conversion, Applicant found ca. 60.5% 6-aminocapronitrile, and 9% hexamethylenediamine; selectivity (defined as in F. Mares, et al., J. Catal., 112, 145–156, 1988) to aminocapronitrile was 86%. At that conversion of the starting dinitrile, byproduct concentration was low: 0.5% of dimers (including bis-hexamethylenetriamine), and trace amounts of other byproducts like hexamethyleneimine and tetrahydroazepine. Selectivity to aminocapronitrile decreased with increasing conversion of the starting dinitrile, for example to 77.5% at 80% conversion.

EXAMPLE 2

The same autoclave as in Example 1 was charged with 20 g of adiponitrile, 200 cc of methanol, 2 g of NaOH solution (50% by wt), 5 g of the Raney Ni 2400 (W. R. Grace Co.) catalyst, and 0.4 g of cyclododecane. Reaction was carried out at 80° C. and 500 psi (3.45 MPa) hydrogen pressure. Total conversion of the starting dinitrile was achieved in 2 h. At 70% adiponitrile conversion Applicant found ca. 58% aminocapronitrile, 11% hexamethylenediamine, and ca. 1.5% total of other byproducts, for selectivity to aminocapronitrile of 83%.

EXAMPLE 3

The reaction was conducted as in Example 2, but twice as much sodium hydroxide was used (i.e., 4 g of the 50% NaOH solution); reaction conditions were 70° C. and 500 psi (3.45 MPa) hydrogen pressure. Selectivity to aminocapronitrile was 89.5% at 70% adiponitrile conversion and was still high at higher levels of adiponitrile conversion, i.e., 82.5% at 80% conversion and 75.5% at 90% conversion.

EXAMPLE 4

The autoclave described in Example 1 was charged with 75 g (0.39 mol) of dodecanedinitrile, 9 g of Raney Ni, Co modified (Degussa BN 113 W), and 0.5 g of cyclododecane. After flushing with nitrogen, 20 cc (0.82 mol) of liquid ammonia was added. The molar ratio of the dinitrile to ammonia was 1:2.1. Hydrogenation was carried out at 80° C and 500 psi (3.45 MPa) total pressure. Selectivity to the aminonitrile was 71% at 50% conversion of the starting dinitrile and decreased as the reaction progressed further, for example, to 63% at 60% conversion of the dinitrile, due to increasing contribution of dodecamethylenediamine, the main byproduct of the hydrogenation reaction.

EXAMPLE 5

The autoclave described in Example 1 was charged with 70 g methylglutaronitrile, 10 g Raney Ni modified with Cr and Fe (W. R. Grace Co, catalyst 2400), 0.5 g cyclododecane standard, and 70 cc of liquid ammonia. The molar ratio of the dinitrile to ammonia was 1:4.45. The hydrogenation reaction was carried out at 60° C. and at 500 psi (3.45 MPa) total pressure. Total conversion of the starting dinitrile was achieved in ca. 3 h, but process was continued for total of 5 h.

Figure 3:
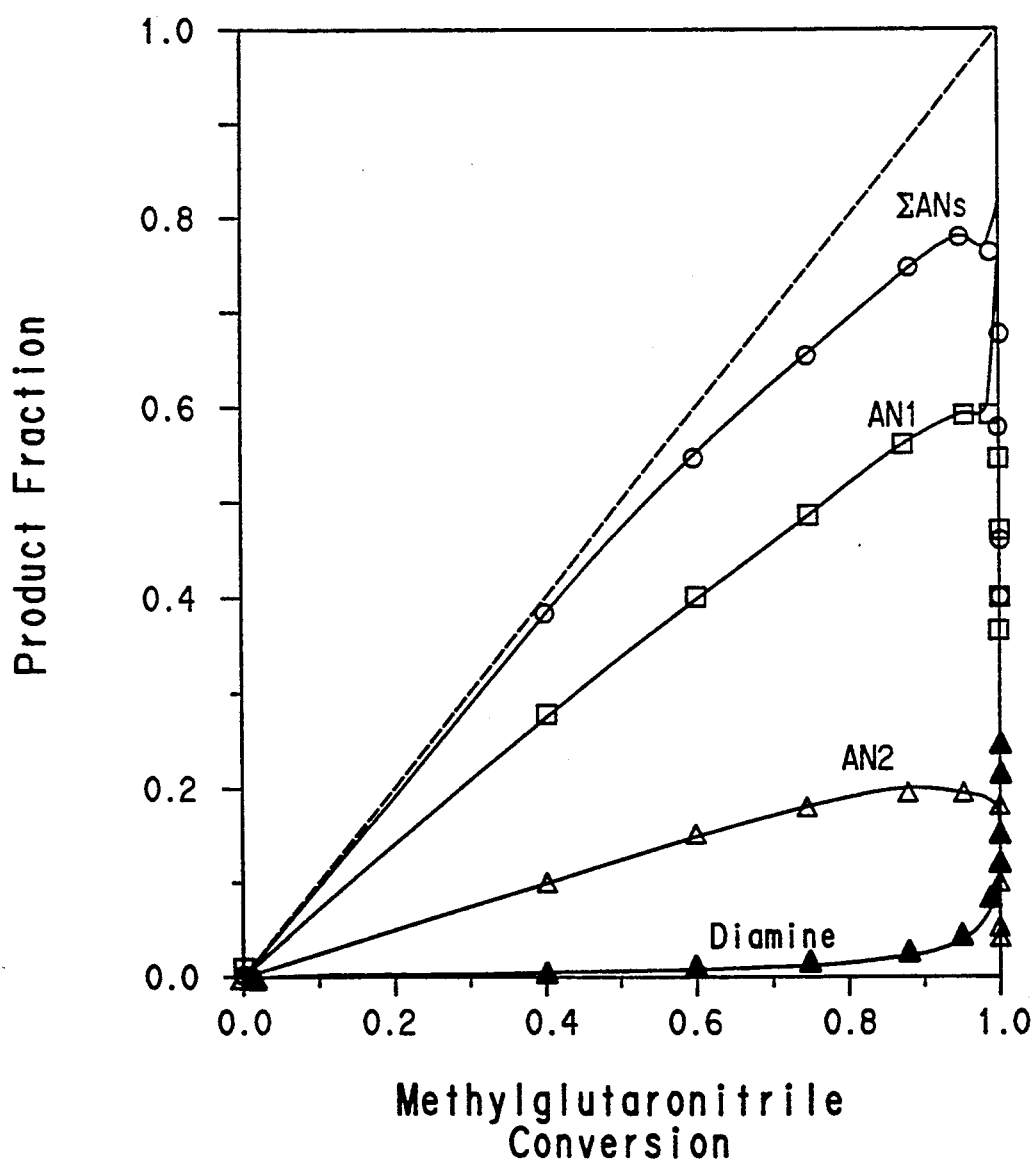
FIG. 3 shows the variation of the concentration of the four main reaction products from the hydrogenation of MGN (1:4.4 in $NH_3$) at 60° C., 500 psi (3.45 MPa) $H_2$ as a function of conversion.

Variation of the concentration of main reaction products with conversion of the starting methylglutaronitrile is shown in FIG. 3. In this Figure "AN 1" represents 5-amino-2-methylvaleronitrile, AN 2 represents 5-amino-4-methylvaleronitrile, "ANs" is the sum of both isomeric forms of aminonitrile, and "MPMD" is methylpentamethylenediamine, the final product of hydrogenation.

Figure 4:
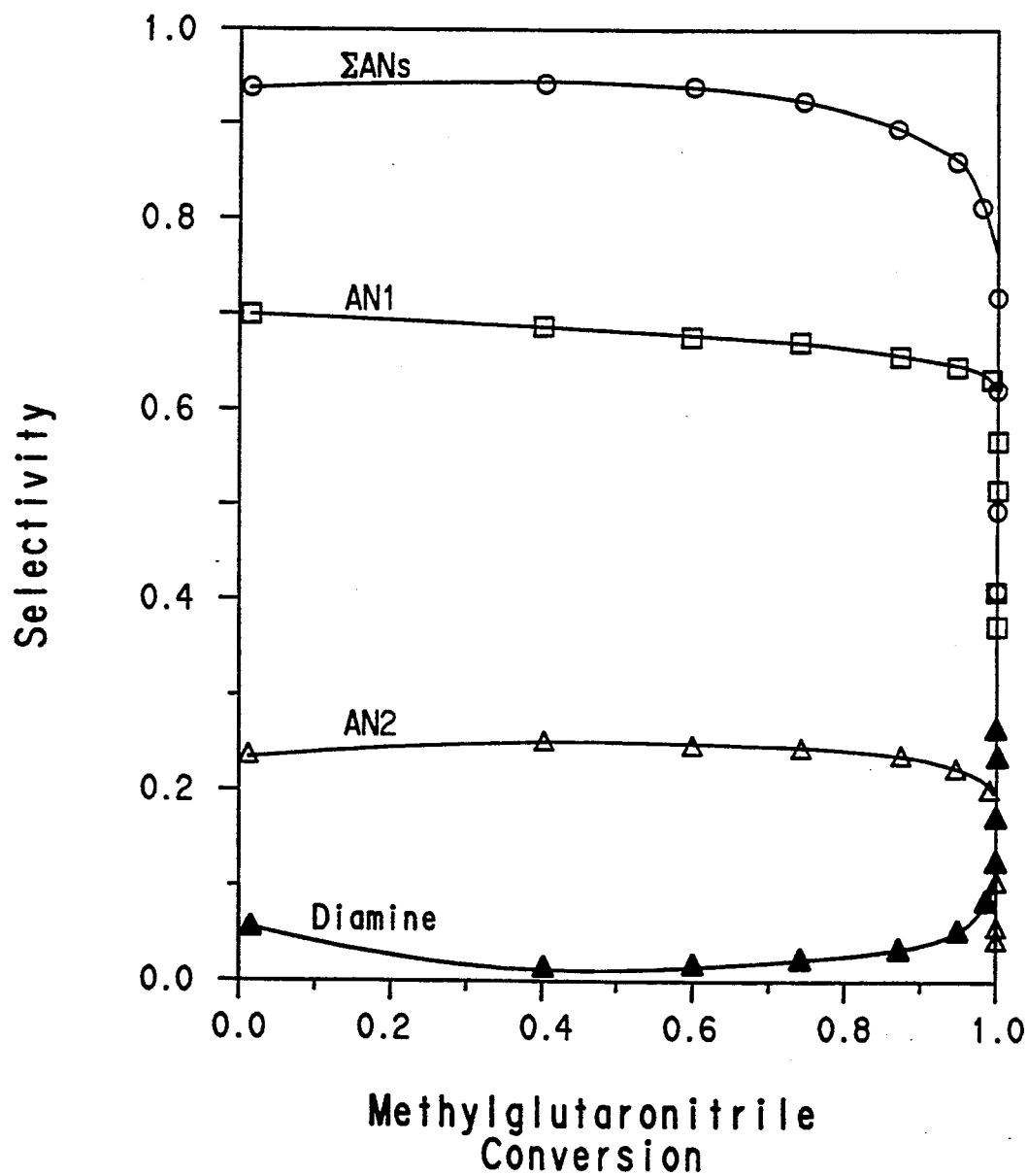
FIG. 4 shows variation in selectivity for the four main products vs. conversion of the starting methylglutaronitrile.

Selectivity of methylglutaronitrile conversion to the main products is shown in FIG. 4. The selectivity to AN 1 is higher than to AN 2. The overall selectivity to aminonitriles (ANs) is 88% at 75% methylglutaronitrile conversion, decreasing with further conversion of the starting dinitrile, but is still 84% at 90% conversion. Selectivities to 3-methylpiperidine and to the diamine are also shown for comparison.

EXAMPLE 6

The autoclave was charged with 20 g adiponitrile, 200 cc tetraglyme (2,5,8,11,14-pentaoxapentadecane), 5 g of the Raney Ni 2400 catalyst, 2.5 g NaOH solution (50%), and 0.5 g cyclododecane, and operated as in Example 2. Reaction was slow, and only 55% conversion of the adiponitrile was reached after 3 h on stream. At that point Applicant found 37.5% aminocapronitrile and 17.5% hexamethylenediamine for selectivity to 6-aminocapronitrile of 68%.

EXAMPLE 7

The same experiment as in Example 6 was repeated using tetrahydrofuran instead of tetraglyme as the solvent. Reaction was slower than observed in Examples 1 and 2, and ca. 92% of the starting dinitrile was converted during 3 h on stream. At 70% adiponitrile conversion Applicant found 43% 6-aminocapronitrile and 27% hexamethylenediamine, for selectivity to 6-aminocapronitrile of 61%.

EXAMPLE 8

The autoclave was charged with 20 g adiponitrile, 200 cc of methanol, and 5 g of Raney Ni 2400 catalyst. No base was added in this test. At 70° C. and 500 psi (3.45 MPa) of hydrogen, only 42% of the starting dinitrile was converted in 3 h of operation. At that point Applicant found 32% of the 6-aminocapronitrile and 2.4% of the hexamethylenediamine, the balance being hexamethyleneimine and products of condensation of the above compounds (formed via elimination of ammonia).

The process described in Example 8 is not suitable for commercial production of 6-aminocapronitrile.

EXAMPLE 9

Methanolic solutions of adiponitrile (at least ten-fold molar excess of the alcohol) are hydrogenated in a well-stirred autoclave at 62° C. ($\pm$ 3) and at hydrogen pressure 1000 psi (i.e., 68 atm, 6.89 MPa), in the presence of a (Cr+Fe) promoted Raney Ni catalyst, representing 12% by weight of the adiponitrile, and in the presence of an inorganic base, such as NaOH, representing 5% by weight of the adiponitrile, and introduced as a 50% solution in water. Agitation of the solution was accomplished using an air-drawn stirrer operated at >1500 rpm. After 2.5 hours of operation, 90% of the starting adiponitrile is converted, with the selectivity to aminonitrile (6-aminocapronitrile) being 82%. Higher selectivities to aminonitrile can be achieved at lower conversions of the adiponitrile.

The process described in Example 9 is suitable for high selectivity of 6-aminocapronitrile.

What is claimed is:

1. A process of selective partial hydrogenation of aliphatic dinitriles to aminonitriles comprising:
   (i) reacting in the presence of hydrogen an aliphatic dinitrile containing 4 to 12 carbons in a reactor at temperatures of from about 25° to 150° C., and at a pressure of from about 50 to 2000 psi in the presence of
      (a) a solvent, said solvent being present in at least a 2:1 molar excess and comprising (i) liquid ammonia or (ii) alcohol of from one to four carbon atoms and containing an inorganic base which is soluble in said alcohol and selected from the group consisting of alkali metal hydroxides, alkali metal methoxides, alkali metal carbonates, alkali earth metal hydroxides, alkali earth metal methoxides and alkali earth metal carbonates; and
      (b) a raney-type catalyst selected from the group consisting of Raney nickel, Raney cobalt, and Raney nickel promoted with metals or metal oxides selected from Group VIB or promoted with the ferrous metals of Group VIII of the Periodic Table; and
   (ii) recovering the corresponding aminonitrile as the major product, selectivity to the aminonitrile increasing to about 95% with decreasing conversion of the starting dinitrile to about 65%.

2. The method of claim 1 wherein the dinitrile is a linear or branched aliphatic diradical containing from 3 to about 12 carbon atoms.

3. The method of claim 2 wherein the dinitrile is a selected from the group consisting of adiponitrile, ethyl succinonitrile, methylglutaronitrile, and dodecanedinitrile.

4. The method of claim 3 wherein the dinitrile is adiponitrile.

5. The method of claim 2 wherein the Raney-type catalyst used is Raney nickel promoted with Cr and Fe in an amount of from about 0.5 to 50.0% by weight of the dinitrile to be hydrogenated.

6. The method of claim 2 wherein the solvent is liquid ammmonia.

7. The method of claim 2 wherein the alcohol is an aliphatic alcohol of one to four carbons.

8. The method of claim 2 wherein the inorganic base is soluble in the alcohol, has a $pK_b$ of less than 5.0, and is present in an amount of between 1 and 10% by weight of the dinitrile to be hydrogenated.

9. The method of claim 8 wherein the inorganic base is selected from the group consisting of LiOH, NaOH, and KOH.

10. The method of claim 8 wherein the temperature is from about 50° to 80° C.

11. The method of claim 2 wherein the pressure is from about 250 to 1000 psi.

12. The method of claim 2 wherein the hydrogenation is carried out as a continuous reaction.

13. A process of selective partial hydrogenation of adiponitrile to 6-aminocapronitrile comprising, reacting a methanolic solution of adiponitrile in the presence of hydrogen, the solution being at least 10:1 molar methanol to adiponitrile, in the presence of Raney nickel in an amount of from 5 to 20% by weight of the adiponitrile used, and further in the presence of an iorganic base from 1 to 10% by weight of the adiponitrile used and introduced as a 50% solution in water;

operating the system at temperatures from about 50° to 80° C., and at pressures from about 250 to 1000 psi; and recovering 6-aminiocapronitrile as the major product selectivity to 6-aminocapronitrile increasing to about 95% with decreasing conversion of the starting dinitrile to about 65%.

14. The method of claim 13 wherein the hydrogenation is carried out as a continuous reaction.

* * * * *